United States Patent
Sakaguchi

(10) Patent No.: US 10,492,757 B2
(45) Date of Patent: Dec. 3, 2019

(54) DIAGNOSTIC IMAGING CATHETER

(71) Applicant: TERUMO KABUSHIKI KAISHA, Shibuya-ku, Tokyo (JP)

(72) Inventor: Yuuki Sakaguchi, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 368 days.

(21) Appl. No.: 15/599,753

(22) Filed: May 19, 2017

(65) Prior Publication Data

US 2017/0333001 A1 Nov. 23, 2017

(30) Foreign Application Priority Data

May 20, 2016 (JP) .................................. 2016-101712

(51) Int. Cl.
| | |
|---|---|
| A61B 8/12 | (2006.01) |
| A61B 8/00 | (2006.01) |
| A61M 25/00 | (2006.01) |
| A61B 5/00 | (2006.01) |
| A61M 25/06 | (2006.01) |
| A61M 25/01 | (2006.01) |
| A61M 39/10 | (2006.01) |

(52) U.S. Cl.
CPC .............. *A61B 8/12* (2013.01); *A61B 5/6852* (2013.01); *A61B 8/4483* (2013.01); *A61B 8/461* (2013.01); *A61M 25/0084* (2013.01); *A61M 25/0097* (2013.01); *A61M 25/01* (2013.01); *A61M 25/0662* (2013.01); *A61M 39/10* (2013.01)

(58) Field of Classification Search
CPC ....... A61B 5/6852; A61B 8/12; A61B 8/4483; A61B 8/461; A61M 25/0084; A61M 25/0097; A61M 25/01; A61M 25/0662; A61M 39/10
See application file for complete search history.

(56) References Cited

U.S. PATENT DOCUMENTS

2014/0371598 A1* 12/2014 Okubo ..................... A61B 8/12
   600/467
2016/0143616 A1* 5/2016 Okubo ..................... A61B 8/12
   600/467

FOREIGN PATENT DOCUMENTS

| JP | 2000-083959 A | 3/2000 |
| JP | 2015-119994 A | 7/2015 |

* cited by examiner

*Primary Examiner* — Michael T Rozanski
(74) *Attorney, Agent, or Firm* — Buchanan Ingersoll & Rooney PC

(57) ABSTRACT

A diagnostic imaging catheter includes a drive shaft provided with a signal transmitting and receiving unit at a distal portion thereof and which is rotatable and movable forward and backward, a sheath into which the drive shaft is inserted, a relay connector coupled to a proximal end of the sheath, a support tube provided at an outer circumference of the drive shaft along an axial direction and which moves forward and backward in conjunction with the drive shaft, a seal member provided inside the relay connector and which seals a space between the relay connector and the support tube, and an injection opening located in a region closer to a distal side than the seal member and closer to a proximal side than a distal end of the support tube in a backward movement limit position thereof and via which a liquid is able to be injected into the sheath.

19 Claims, 8 Drawing Sheets

DIAGNOSTIC IMAGING CATHETER

CROSS-REFERENCE TO RELATED APPLICATION

This application claims priority to Japanese Application No. 2016-101712 filed on May 20, 2016, the entire content of which is incorporated herein by reference.

TECHNICAL FIELD

The disclosure herein relates to a diagnostic imaging catheter.

BACKGROUND ART

Heretofore, as a medical device that is used to acquire a diagnostic image to diagnose, for example, a lesion area in the living body, there is a diagnostic imaging catheter that is used in an imaging apparatus for diagnosis using, for example, intravascular ultrasound (IVUS) or optical coherence tomography (OCT).

The diagnostic imaging catheter is equipped with a drive shaft, which is provided with a transmitting and receiving unit that transmits and receives inspection waves, and a sheath, into which the drive shaft is inserted in such a manner as to be movable forward and backward. During the use of the diagnostic imaging catheter, what is called a pullback operation (an inward pulling operation) is performed which moves the drive shaft from a distal side to a proximal side by moving the drive shaft backward while rotating the drive shaft, or a push-in operation is performed which pushes the drive shaft into the distal side (refer to Japanese Patent Application Publication No. 2015-119994).

When the diagnostic imaging catheter is used, the inside of the sheath is filled with a priming liquid such as a physiological salt solution (a priming process) so as to efficiently transmit and receive inspection waves. To fill the inside of the sheath with the priming liquid, a syringe is usually connected to a port provided at a hub on the hand side, and the priming liquid is injected into the sheath. Then, the injected priming liquid flows toward the distal side through a gap between the sheath and the drive shaft and is thus discharged from a communicating hole provided at the distal end of the sheath to the outside of the catheter.

The pushing force necessary on the syringe to inject the priming liquid depends on the flow path resistance in a flow path through which the priming liquid flows. In other words, as the flow path resistance is larger, a larger pushing force is required on the syringe. Therefore, in order to smoothly perform the priming process, it is desirable to reduce the flow path resistance. Here, the flow path resistance is inversely proportionate to the diameter of the flow path through which the priming liquid flows and is proportionate to the length of the flow path through which the priming liquid flows.

While examples of the method for reducing the flow path resistance include increasing a gap (flow path diameter) between the sheath and the drive shaft, increasing the gap may cause the vibration of the transmitting and receiving unit occurring during the rotation of the drive shaft to become large, so that an image may not be able to be appropriately acquired.

Based upon the above, a diagnostic imaging catheter is needed which allows the priming process to be smoothly performed by reducing the flow path resistance without increasing the gap between the sheath and the drive shaft.

In relation to this, for example, Japanese Patent Application Publication No. 2000-083959 discloses a diagnostic imaging catheter in which a priming port is provided at a unit connector (corresponding to a sheath connector) provided at the distal side of a hub (corresponding to a drive shaft connector). According to the diagnostic imaging catheter disclosed therein, since the length of a flow path through which a priming liquid flows is shorter than that in a diagnostic imaging catheter in which the port is provided at the hub, the flow path resistance can be reduced.

However, with respect to a diagnostic imaging catheter according to Japanese Patent Application Publication No. 2000-083959, in order to smoothly perform a priming process, a further reduction of the flow path resistance is demanded.

One consideration though, is that if the priming liquid directly contacts the drive shaft during the priming process, the drive shaft may be, for example, deformed or damaged, so that an image may not be able to be appropriately acquired.

In view of the above-mentioned problems, the disclosure herein provides a diagnostic imaging catheter which allows a priming process to be smoothly performed by reducing the flow path resistance without increasing a gap between the sheath and the drive shaft, while preventing a priming liquid from contacting the drive shaft to disable appropriately acquiring an image.

SUMMARY

A diagnostic imaging catheter according to an exemplary embodiment of the disclosure includes a drive shaft which is provided with a signal transmitting and receiving unit at a distal portion thereof and which is rotatable and movable forward and backward, a sheath into which the drive shaft is inserted, a relay connector which is coupled to a proximal end of the sheath, a support tube which is provided at an outer circumference of the drive shaft along an axial direction and which moves forward and backward in conjunction with the drive shaft, a seal member which is provided inside the relay connector and which seals a space between the relay connector and the support tube, and an injection opening which is located in a region closer to a distal side than the seal member and closer to a proximal side than a distal end of the support tube in a backward movement limit position thereof and via which a liquid is able to be injected into the sheath.

According to the diagnostic imaging catheter configured as described above, a priming liquid is injected via the injection opening, which is located in the region closer to the distal side than the seal member, which is provided inside the relay connector. Therefore, the length of the flow path through which the priming liquid flows is short as compared with a configuration in which a port is provided at a unit connector or a hub, and the flow path resistance is thus reduced. Accordingly, the priming process can be smoothly performed by reducing the flow path resistance without increasing the gap between the sheath and the drive shaft. Moreover, since the injection opening is located closer to the proximal side than the distal end of the support tube in the backward movement limit position thereof, when the priming liquid is injected via the injection opening, the priming liquid contacts the support tube, which is provided at the outer circumference of the drive shaft. Therefore, the priming liquid can be prevented from contacting the drive shaft to hinder appropriately acquiring an image.

With the above-described configuration, a diagnostic imaging catheter can be provided which allows the priming process to be smoothly performed by reducing the flow path resistance without increasing a gap between the sheath and the drive shaft, while preventing the priming liquid from contacting the drive shaft and hindering appropriately acquiring an image.

BRIEF DESCRIPTION OF THE DRAWINGS

FIGS. 2A and 2B are diagrams schematically illustrating the entire configuration of the diagnostic imaging catheter according to an exemplary embodiment of the disclosure, in which FIG. 2A is a side view of the diagnostic imaging catheter before a pullback operation (an inward pulling operation) is performed and FIG. 2B is a side view of the diagnostic imaging catheter when the pullback operation is being performed.

DETAILED DESCRIPTION

Figure 1:
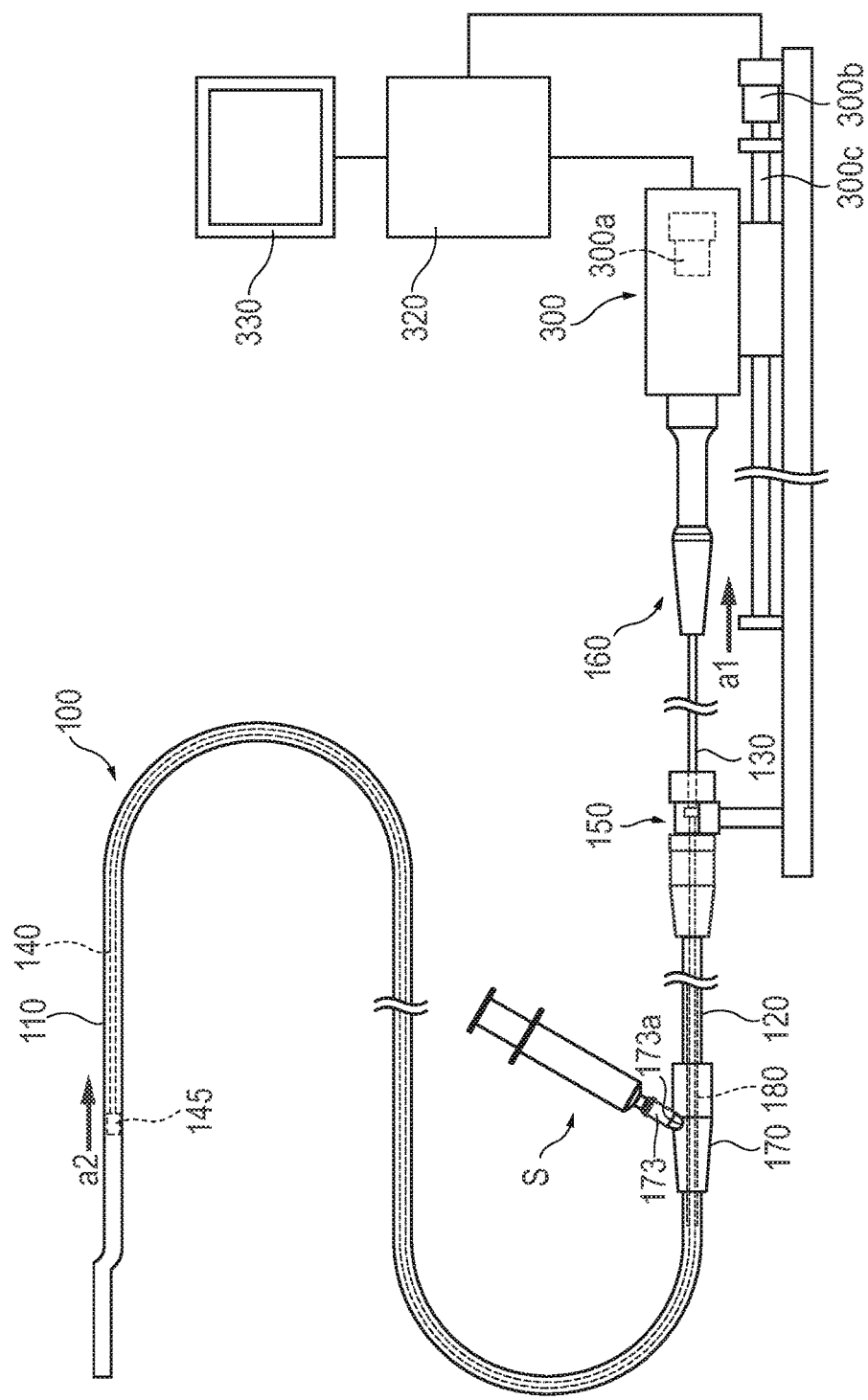
FIG. 1 is a plan view illustrating a state in which an external apparatus is connected to a diagnostic imaging catheter according to an exemplary embodiment of the disclosure.

Hereinafter, embodiments of the disclosure will be described with reference to the accompanying drawings. Furthermore, the following description should not be construed to limit the technical scope set forth in the claims or the meanings of terms. Moreover, dimensional ratios illustrated in the drawings are exaggerated for the purpose of illustration and may be different from the actual ratios.

Figure 2A:
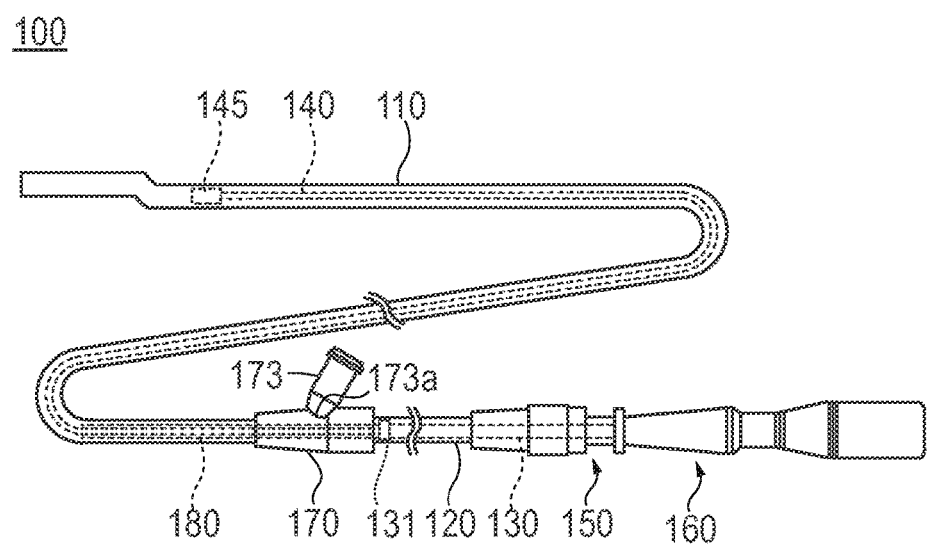
Figure 2B:
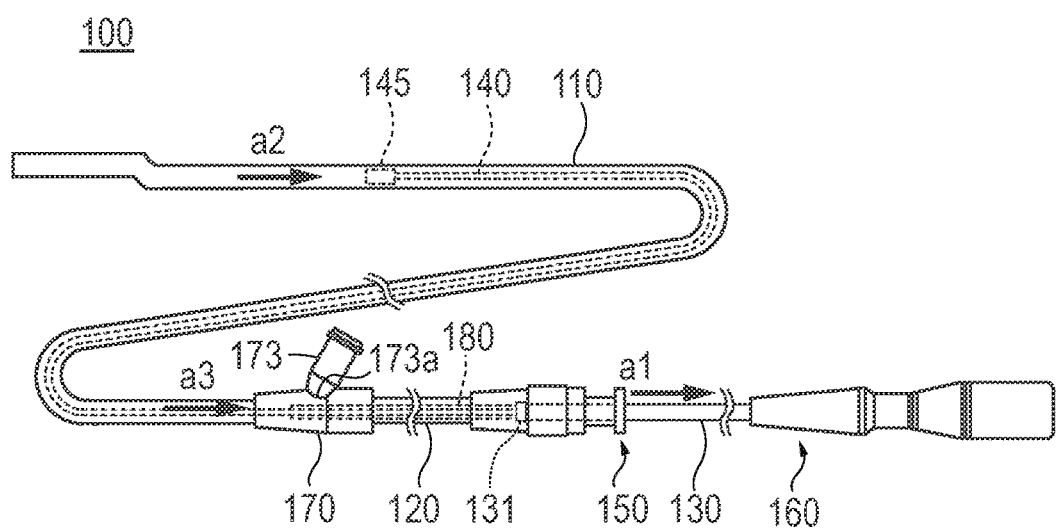
Figure 3:
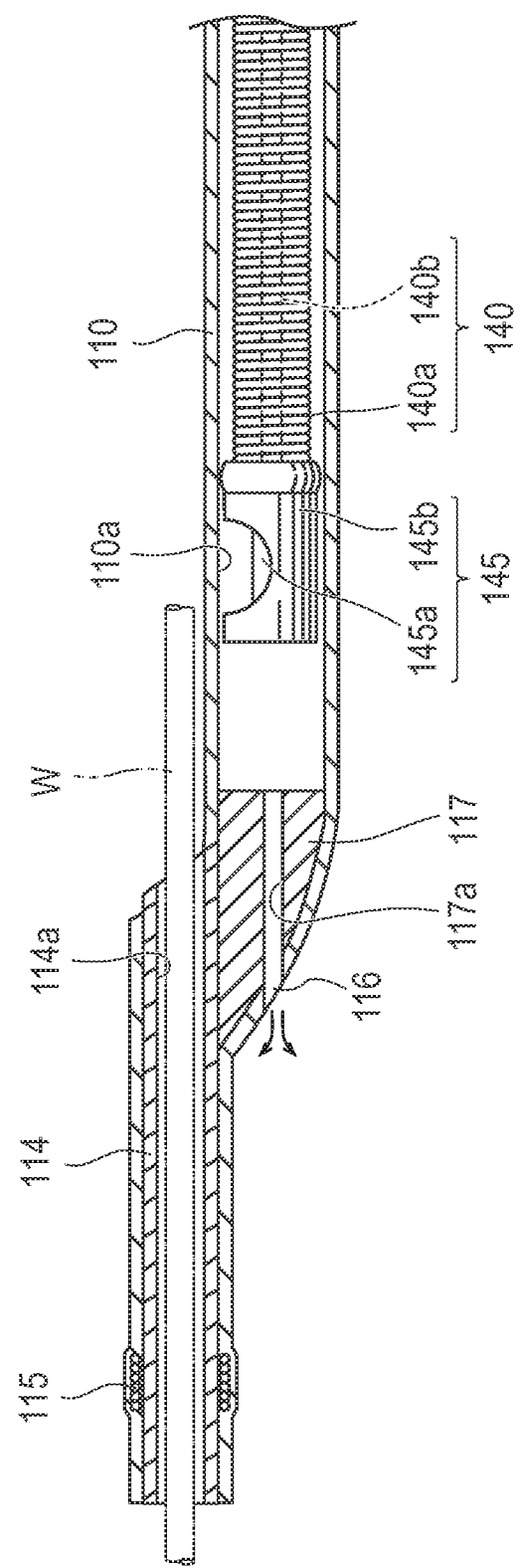
FIG. 3 is an enlarged sectional view thereof illustrating a configuration of a distal side of the diagnostic imaging catheter.
Figure 4:
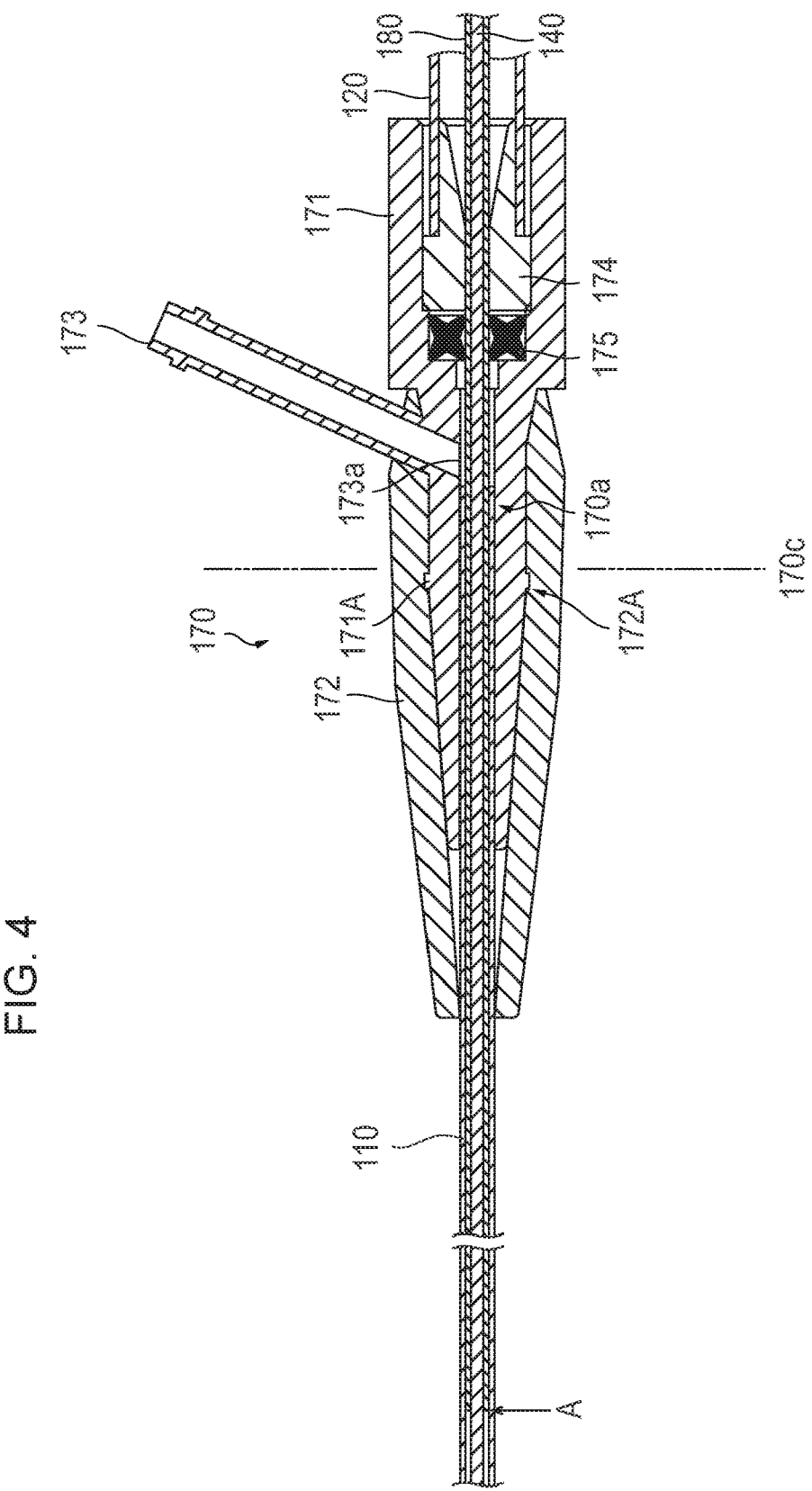
FIG. 4 is an enlarged sectional view thereof illustrating a configuration of a portion near a relay connector in a state in which a support tube is in a forward movement limit position.
Figure 5:
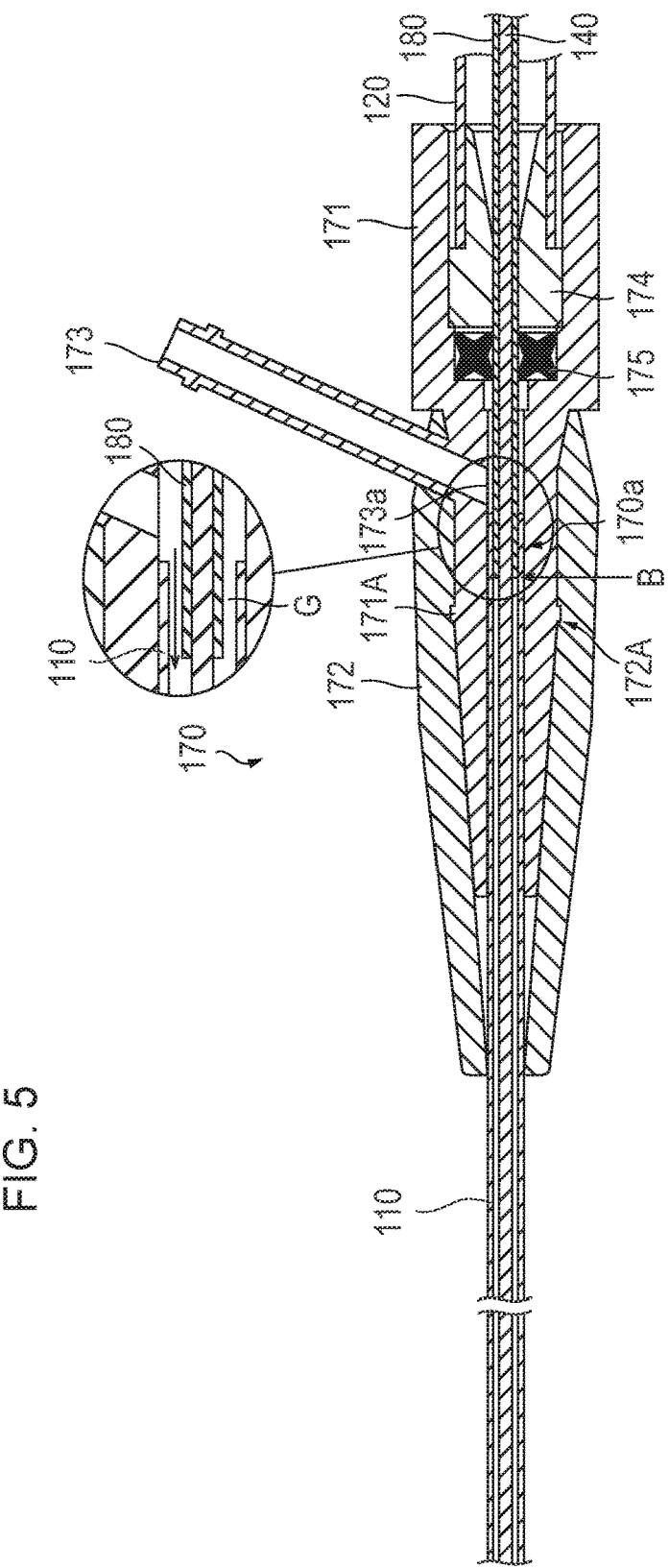
FIG. 5 is an enlarged sectional view thereof illustrating a configuration of the portion near the relay connector in a state in which the support tube is in a backward movement limit position.
Figure 6:
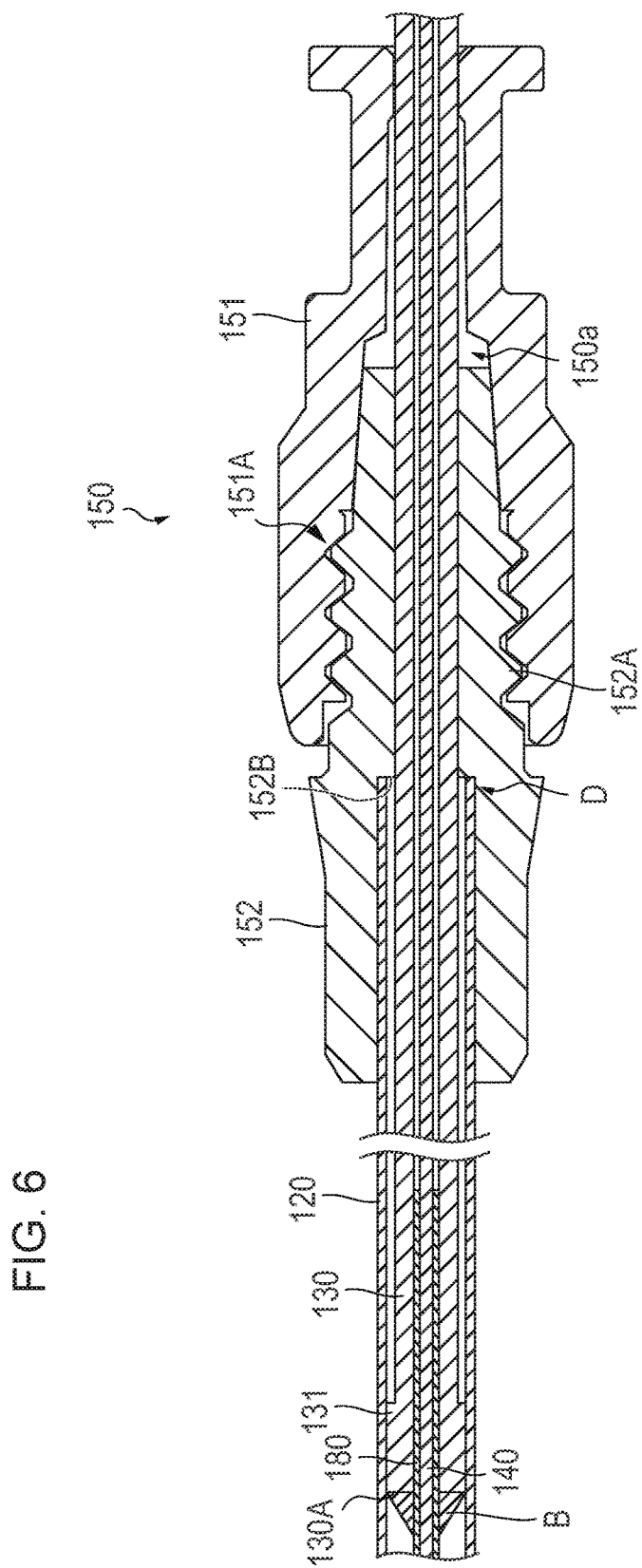
FIG. 6 is an enlarged sectional view thereof illustrating a configuration of a portion near a unit connector.
Figure 7:
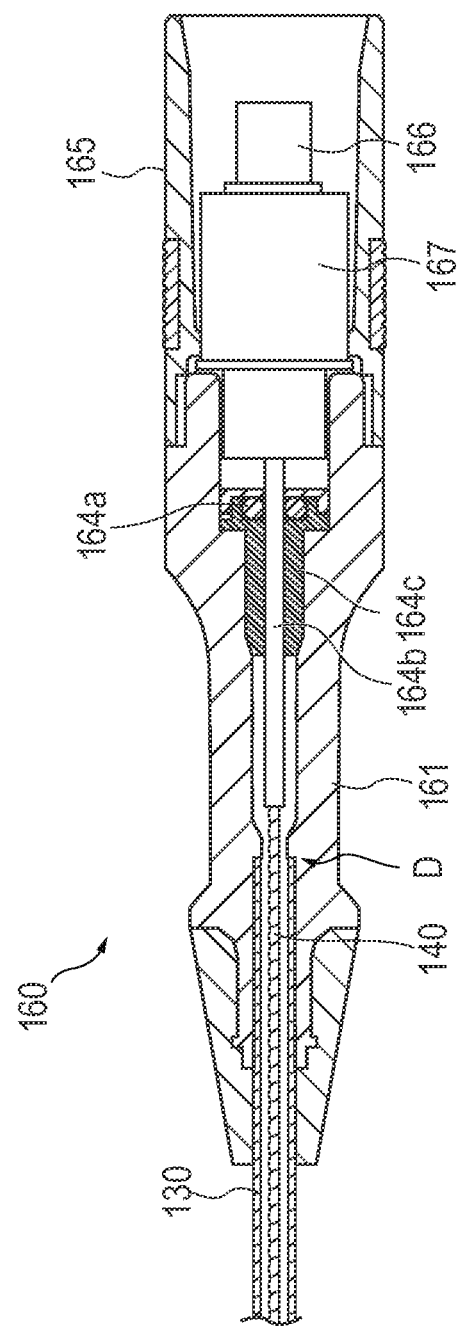
FIG. 7 is an enlarged sectional view thereof illustrating a configuration of a proximal side of the diagnostic imaging catheter.

FIG. 1 is a plan view illustrating a state in which an external apparatus 300 is connected to a diagnostic imaging catheter 100 according to an exemplary embodiment of the disclosure, FIGS. 2A and 2B are diagrams schematically illustrating the entire configuration of the diagnostic imaging catheter 100, FIG. 3 is a diagram illustrating a configuration of a distal side of the diagnostic imaging catheter 100, FIG. 4 and FIG. 5 are diagrams illustrating a configuration of a portion near a relay connector 170, FIG. 6 is a diagram illustrating a configuration of a portion near a unit connector 150, and FIG. 7 is a diagram illustrating a configuration of a proximal side of the diagnostic imaging catheter 100.

The diagnostic imaging catheter 100 according to the exemplary embodiment may be applied to intravascular ultrasound (IVUS). As illustrated in FIG. 1, the diagnostic imaging catheter 100 is driven while being connected to the external apparatus 300.

As illustrated in FIG. 1 and FIGS. 2A and 2B, the diagnostic imaging catheter 100 includes, in broad terms, a sheath 110, which is inserted into a body cavity in the living body, an outer tube 120, which is provided at a proximal side of the sheath 110, an inner shaft 130, which is inserted into the outer tube 120 in such a way as to be movable forward and backward, a drive shaft 140, which is equipped with a transducer unit 145 configured to transmit and receive signals at a distal end of the drive shaft 140, and which is provided in such a way as to be rotatable and movable forward and backward inside the sheath 110, a relay connector 170, which interconnects the sheath 110 and the outer tube 120, a support tube 180, which is provided on an outer circumference of the drive shaft 140 along an axial direction and which moves forward and backward in conjunction with the drive shaft 140, a unit connector 150, which is provided at a proximal side of the outer tube 120 and which is configured to hold the inner shaft 130 inside, and a hub 160, which is provided on a proximal side of the inner shaft 130.

In the context of the disclosure, a side of the diagnostic imaging catheter 100 which is inserted into a body cavity is referred to as a distal end or a distal side, a side of the diagnostic imaging catheter 100 on which the hub 160 is provided is referred to as a proximal end or a proximal side, and an extending direction of the outer tube 120 is referred to as an axial direction.

As illustrated in FIG. 2A, the drive shaft 140 extends up to the inside of the hub 160 through the sheath 110, the relay connector 170, the support tube 180, the outer tube 120, the inner shaft 130, and the unit connector 150.

The hub 160, the inner shaft 130, the drive shaft 140, the transducer unit 145, and the support tube 180 are interconnected in such a way as to be integrally movable forward and backward in the axial direction. Therefore, when an operation to push the hub 160 toward the distal side is performed, the inner shaft 130 connected to the hub 160 is pushed into the outer tube 120 and the unit connector 150, the drive shaft 140 and the transducer unit 145 are moved inside the sheath 110 toward the distal side, and the support tube 180 is moved inside the relay connector 170 toward the distal side. For example, when an operation to pull the hub 160 toward the proximal side is performed, the inner shaft 130 is pulled out of the outer tube 120 and the unit connector 150 as indicated by an arrow a1 in FIG. 1 and FIG. 2B, the drive shaft 140 and the transducer unit 145 are moved inside the sheath 110 toward the proximal side as indicated by an arrow a2, and the support tube 180 is moved inside the relay connector 170 toward the proximal side as indicated by an arrow a3.

As illustrated in FIG. 2A, when the inner shaft 130 is pushed toward the distal side to a maximum extent, a distal portion of the inner shaft 130 reaches the vicinity of the relay connector 170. At this time, the transducer unit 145 is located in the vicinity of the distal end of the sheath 110.

As illustrated in FIG. 2B, a falling-out preventive protrusion 131 (see FIG. 6) is provided at a distal end of the inner shaft 130. The falling-out preventive protrusion 131 has the function of preventing the inner shaft 130 from falling out of the outer tube 120. The falling-out preventive protrusion 131 is configured to engage an inner wall 152B (see FIG. 6) of the unit connector 150 when the hub 160 is pulled toward the proximal side to a maximum extent, in other words, when the inner shaft 130 is pulled out of the outer tube 120 and the unit connector 150 to a maximum extent. Moreover, even when the hub 160 is pulled toward the proximal side to a maximum extent, the support tube 180 is located closer to the distal side than an injection opening 173a, which is described below (see a position indicated by reference character B in FIG. 5).

As illustrated in FIG. 3, the drive shaft 140 includes a pipe body 140a having flexibility, and a signal line 140b which is inserted through the pipe body 140a. The pipe body 140a can be configured with, for example, multiple layers of coils having different winding directions around the axis. Examples of the material of the coils include stainless steel and a nickel-titanium (Ni—Ti) alloy. The signal line 140b can be configured with, for example, a twisted pair cable or a coaxial cable.

The transducer unit 145 includes an ultrasound transducer (corresponding to a signal transmitting and receiving unit) 145a, which transmits and receives ultrasound waves, and a housing 145b, which contains the ultrasound transducer 145a.

The ultrasound transducer 145a has the function of transmitting ultrasound waves, which serve as inspection waves, into a body cavity, and receiving ultrasound waves reflected from the body cavity. The ultrasound transducer 145a is electrically connected to an electrode terminal 166 (see FIG. 7) via the signal line 140b.

The ultrasound transducer 145a can be made from a piezoelectric material, such as ceramic or a crystal.

As illustrated in FIG. 3, the sheath 110 is equipped with a lumen 110a, into which the drive shaft 140 is inserted in such a way as to be movable forward and backward. A guide wire insertion member 114, which is equipped with a guide wire lumen 114a into which a guide wire W is able to be inserted, is attached to a distal portion of the sheath 110 in such a way to be arranged in parallel with the lumen 110a provided in the sheath 110. The sheath 110 and the guide wire insertion member 114 can be configured in an integrated fashion with the use of, for example, heat-welding. The guide wire insertion member 114 is provided with a marker 115 having a radiopaque property. The marker 115 is configured with a metal coil having a high radiopaque property, such as Pt, Au, or Ir.

A communicating hole 116, through which the inside of the lumen 110a communicates with the outside thereof, is formed at the distal portion of the sheath 110. Moreover, a reinforcement member 117, which is used to rigidly join and support the guide wire insertion member 114, is provided at the distal portion of the sheath 110. The reinforcement member 117 is provided with a communicating passage 117a, through which the communicating hole 116 communicates with the inside of the lumen 110a that is located closer to the proximal side than the reinforcement member 117. Furthermore, the distal portion of the sheath 110 does not necessarily need to be provided with the reinforcement member 117.

The communicating hole 116 is a priming liquid discharge hole through which the priming liquid can be discharged. When using the diagnostic imaging catheter 100, the operator performs a priming process to fill the inside of the sheath 110 with the priming liquid so as to reduce the attenuation of ultrasound waves caused by air inside the sheath 110 and to efficiently transmit and receive ultrasound waves. When the priming process is performed, the priming liquid is released to the outside through the communicating hole 116, so that a gas such as air can be discharged from the inside of the sheath 110 together with the priming liquid.

The sheath 110 is formed of a material having a high ultrasound transmissivity. In a preferred embodiment, the distal portion of the sheath 110, defined by the range of where the ultrasound transducer 145a can move in the axial direction of the sheath 110, forms an acoustic window portion having ultrasound transmissivity higher than those of other portions of the sheath 110.

The sheath 110, the guide wire insertion member 114, and the reinforcement member 117 are formed of a material having flexibility, and the material is not limited to a specific material. Examples of the material include various thermoplastic elastomers, such as a styrene elastomer, a polyolefin elastomer, a polyurethane elastomer, a polyester elastomer, a polyamide elastomer, a polyimide elastomer, a polybutadiene elastomer, a trans-polyisoprene elastomer, a fluororubber elastomer, and a chlorinated polyethylene elastomer. A combination of one or two or more (polymer alloy, polymer blend, or laminated body) of these elastomers can also be used as the material. Furthermore, a hydrophilic lubricant coating layer which exhibits lubricating ability at the time of wetting can be arranged on the outer surface of the sheath 110.

As illustrated in FIG. 4 and FIG. 5, the relay connector 170 interconnects the sheath 110 and the outer tube 120. The relay connector 170 includes an outer tube holding portion 171, which is provided on the proximal side, an anti-kink protector 172, which is provided on the distal side, and a port 173, which communicates with the injection opening 173a through which a priming liquid is able to be injected. The relay connector 170 is equipped with a lumen 170a, into which the drive shaft 140 and the support tube 180 are inserted in such a way as to be movable forward and backward.

The outer tube holding portion 171 is inserted into the anti-kink protector 172 at the distal side and is fixed in such a manner that a convex portion 171A, which is provided on the outer circumference of the outer tube holding portion 171, is fitted in a concave portion 172A, which is provided on the inner circumference of the anti-kink protector 172. Thus, the outer tube holding portion 171 is fixedly connected to the anti-kink protector 172.

A bearing 174, which supports the drive shaft 140 and the support tube 180, is provided on the inside of the outer tube holding portion 171. The outer tube holding portion 171 holds the outer tube 120 in cooperation with the bearing 174.

Moreover, an X-ring (corresponding to a seal member) 175, which seals a space between the outer tube holding portion 171 and the support tube 180, is provided on the inside of the outer tube holding portion 171 and on the distal side of the bearing 174. Therefore, when the priming liquid is injected, the priming liquid can be prevented from flowing toward the proximal side between the outer tube holding portion 171 and the support tube 180. The configuration for sealing a space between the outer tube holding portion 171 and the support tube 180 is not limited to the illustrated X-ring, but can be, for example, an O-ring. The material used to configure the outer tube holding portion 171 can include a relatively hard resin material.

The anti-kink protector 172 is mounted for the purpose of smoothing a variance in hardness at a connection portion between the sheath 110 and the outer tube holding portion 171, which differ greatly in hardness. Therefore, it is desirable that the anti-kink protector 172 be formed of a material having a hardness lower than that of the outer tube holding portion 171. In this way, providing the anti-kink protector 172 enables preventing, for example, bends and kinks of the sheath 110 in a portion at which the sheath 110 is exposed from the outer tube holding portion 171. Furthermore, while, in the exemplary embodiment, the anti-kink protector 172 is configured as a member separate from the outer tube holding portion 171, the configuration is not specifically limiting and the anti-kink protector 172 can be configured integrally with the outer tube holding portion 171 and configured in a spiral cut shape.

As illustrated in FIG. 4, when the support tube 180 is located in a forward movement limit position (see a position indicated by reference character A in FIG. 4), the sheath 110, the drive shaft 140, and the support tube 180 are in a state of being pulled out of the inside of the anti-kink protector 172 toward the distal side. Moreover, as illustrated in FIG. 5, when the support tube 180 is located in a backward movement limit position (see a position indicated by reference character B in FIG. 5), the sheath 110 and the drive shaft 140 are in a state of being pulled out of the inside of the anti-kink protector 172 toward the proximal side.

As illustrated in FIG. 4 and FIG. 5, the port 173 is configured integrally with the outer tube holding portion 171. According to this configuration, since the port 173 is made from a relatively hard material, the port 173 is unlikely to deform when the syringe S is connected thereto, as compared with a case where a port is configured integrally with an anti-kink protector. The port 173 communicates with the injection opening 173a, and the injection opening 173a communicates with the lumen 170a. When the priming process is performed, the syringe S (see FIG. 1) is connected to the port 173.

In this way, since the injection opening 173a is provided at the relay connector 170, the port 173 is provided at a position closer to the distal side than in a configuration in which a port for priming is provided, for example, at a hub or a unit connector as in the prior art. Accordingly, the length of the flow path through which the priming liquid flows up to the communicating hole 116 is small so as to reduce the flow path resistance and to enable smoothly performing the priming process, so that a burden on the operator can be decreased. Moreover, the length of the flow path through which the priming liquid flows up to the communicating hole 116 being small enables decreasing the injected amount of the priming liquid. Therefore, since the amount of action required by the operator to push the syringe S when injecting the priming liquid is decreased, the priming process can be smoothly performed and, thus, a burden on the operator can be decreased.

Furthermore, a plurality of protrusions or step differences D (see FIG. 6 and FIG. 7) is configured in a lumen leading from the hub 160 to the relay connector 170. The step difference D illustrated in FIG. 6 is configured for the purpose of causing the falling-out preventive protrusion 131 to be engaged and stop there, and the step difference D illustrated in FIG. 7 is configured for the purpose of receiving and holding the inner shaft 130. For example, in the case of a configuration in which a port for priming is provided at a hub, when the priming liquid passes the step difference D, a whirlpool may occur to cause air bubbles. Then, when the air bubbles together with the priming liquid moves to the distal side of the sheath 110 and attaches to the transducer unit 145 (air trap), the propagation of ultrasound is blocked and a signal measured by the transducer unit 145 becomes weak, so that an image may not be able to be appropriately acquired. However, in the case of the diagnostic imaging catheter 100 according to the exemplary embodiment herein, since the port 173 is provided at the relay connector 170, such a phenomenon that the priming liquid passes the step difference D and flows toward the distal side does not occur. Accordingly, the occurrence of such an air trap as mentioned above can be adequately prevented.

Moreover, for example, in the case of a configuration in which the port is provided at a hub, a protrusion is required to be provided at the hub so as to determine the direction of the hub when the hub is connected to the external apparatus 300. On the other hand, in the case of the diagnostic imaging catheter 100 according to the exemplary embodiment herein, since the injection opening 173a is provided at the relay connector 170, the above-mentioned protrusion is not required.

The port 173 is configured to be inclined from the direction perpendicular to the axial direction toward the proximal side, as illustrated in FIG. 4. This configuration, when the priming liquid is injected, enables the priming liquid to flow toward the distal side through the injection opening 173a, as compared with a configuration in which a port is provided along the direction perpendicular to the axial direction. Therefore, the force with which the operator pushes the syringe S can be decreased.

The injection opening 173a is located on the distal side of the X-ring 175 and closer to the proximal side than the center 170c of the relay connector 170 in the axial direction. According to this configuration, the injection opening 173a is configured in the vicinity of the X-ring 175. Therefore, air trapped between the injection opening 173a and the X-ring 175 can be reduced.

As illustrated in FIG. 4 to FIG. 6, the support tube 180 is provided on the outer circumference of the drive shaft 140 and the inner circumference of the relay connector 170 along the axial direction, thus covering and protecting the drive shaft 140.

As illustrated in FIG. 4 and FIG. 5, the support tube 180 is configured to be sandwiched between the sheath 110 and the drive shaft 140 at the distal side. As illustrated in FIG. 6, the support tube 180 is configured to be sandwiched between the inner shaft 130 and the drive shaft 140 at the proximal side.

As illustrated in FIG. 6, the support tube 180 is bonded to the inner shaft 130 with adhesive B at the distal portion 130A of the inner shaft 130. Accordingly, the support tube 180 is configured to be movable forward and backward in the axial direction in conjunction with the inner shaft 130.

As illustrated in FIG. 5, when the hub 160 is pulled toward the proximal side to a maximum extent (corresponding to the backward movement limit position of the support tube 180), the support tube 180 is located closer to the distal side than the injection opening 173a. In other words, the injection opening 173a is located closer to the proximal side than the distal end (a position indicated by reference character B in FIG. 5) of the support tube 180 in the backward movement limit position. According to this configuration, the priming liquid injected via the injection opening 173a contacts the support tube 180 without directly contacting the drive shaft 140. Accordingly, the drive shaft 140 can be prevented from deforming due to the priming liquid contacting the drive shaft 140. Moreover, since the support tube 180 covers the drive shaft 140 at the injection opening 173a, when the drive shaft 140 is rotated to acquire an image, the drive shaft 140 can be prevented from entering the injection opening 173a and winding in a twisted or contorted shape. The material used to configure the support tube 180 is, for example, a resin material.

It is desirable that, as illustrated in FIG. 5, the distal end of the support tube 180 in the backward movement limit position be located closer to the injection opening 173a. According to this configuration, the length in the axial direction of a portion forming a gap G between the sheath 110 and the support tube 180 becomes small. Since the portion forming the gap G is a portion that is relatively high in flow path resistance in the flow path through which the priming liquid flows, the length of the gap G in the axial direction becoming small enables smoothly performing the priming process.

As illustrated in FIG. 6, the unit connector 150 includes a unit connector body 151, which is provided at the proximal side, and a cover member 152, which is provided at the distal side. The unit connector 150 is equipped with a lumen 150a, into which the inner shaft 130 and the drive shaft 140 are inserted in such a way as to be movable forward and backward.

A female screw portion 151A having a groove is provided on the internal surface of the distal side of the unit connector body 151. A male screw portion 152A having a thread is provided on the external surface of the proximal side of the cover member 152. The unit connector body 151 is configured to be able to be attached to the cover member 152 by the female screw portion 151A of the unit connector body 151 being screwed on the male screw portion 152A of the cover member 152.

The outer tube 120 attached to the relay connector 170 is inserted into the cover member 152, and the inner shaft 130 and the drive shaft 140, which extend from the hub 160, are inserted into the outer tube 120.

The material used to configure the unit connector body 151 and the cover member 152 can be a relatively hard resin material.

As illustrated in FIG. 7, the hub 160 includes a hub body 161, which has a hollow shape, a connection pipe 164b, which holds the drive shaft 140, a sealing member 164a, which seals a space between the hub body 161 and the connection pipe 164b, a bearing 164c, which rotatably supports the connection pipe 164b, and a connector portion 165, inside which an electrode terminal 166 that is mechanically and electrically connectable to the external apparatus 300 is mounted.

The inner shaft 130 is connected to the distal portion of the hub 161. The drive shaft 140 is pulled out of the inner shaft 130 inside the hub body 161.

The connection pipe 164b holds the drive shaft 140 at the distal end of the connection pipe 164b, which is an end portion opposite to a rotor 167, so as to transmit the rotation of the rotor 167 to the drive shaft 140. A seal member (not illustrated) is provided between the connection pipe 164b and the drive shaft 140. Therefore, the priming liquid can be prevented from flowing toward the proximal side and then contacting the rotor 167.

The signal line 140b (see FIG. 3) is inserted through the connection pipe 164b, and one end of the signal lime 140b is connected to the electrode terminal 166 and the other end thereof is connected to the ultrasound transducer 145a through the inside of the drive shaft 140. A received signal acquired by the ultrasound transducer 145a is transmitted to the external apparatus 300 via the electrode terminal 166, and is then subjected to predetermined processing to be displayed as an image.

The sealing member 164a is, for example, an O-ring, and restrains the priming liquid from moving toward the proximal side in the hub 160 during the priming process. Therefore, the priming liquid can be prevented from flowing toward the proximal side and contacting the rotor 167. Moreover, while air bubbles present in a lumen between the injection opening 173a and the sealing member 164a move toward the proximal side due to a priming injection pressure applied when priming is performed, providing the sealing member 164a prevents the air bubbles from moving toward the proximal side beyond the sealing member 164a.

Referring back to FIG. 1, the diagnostic imaging catheter 100 is connected to and driven by the external apparatus 300.

As described above, the external apparatus 300 is connected to the connector portion 165 (see FIG. 7) provided at the proximal side of the hub 160.

Furthermore, the external apparatus 300 includes a motor 300a, which is a power source to rotate the drive shaft 140, and a motor 300b, which is a power source to move the drive shaft 140 in the axial direction. The rotational motion of the motor 300b is converted into an axial motion by a ball screw 300c connected to the motor 300b.

The operation of the external apparatus 300 is controlled by a control apparatus 320 that is electrically connected to the external apparatus 300. The control apparatus 320 includes a central processing unit (CPU) and a memory as main constituent elements. The control apparatus 320 is electrically connected to a monitor 330.

Next, an example of using the diagnostic imaging catheter 100 according to the exemplary embodiment is described.

First, with the hub 160 pulled toward the proximal side to a maximum extent (see FIG. 2B and FIG. 5), the operator connects the syringe S filled with the priming liquid to the port 173, and the operator pushes the plunger of the syringe S. In response to the plunger of the syringe S being pushed, the priming liquid is injected into the relay connector 170 via the injection opening 173a.

In the case of the diagnostic imaging catheter 100 according to the exemplary embodiment, since the injection opening 173a is provided at the relay connector 170, the length of the flow path through which the priming liquid flows up to the communicating hole 116 is short as compared with a configuration in which a port is provided at a unit connector or a hub, and thus the flow path resistance is reduced. Moreover, since the support tube 180 is located closer to the distal side than the injection opening 173a, the priming liquid injected via the injection opening 173a contacts the support tube 180 without directly contacting the drive shaft 140. Accordingly, the drive shaft 140 can be prevented from deforming due to the force of the priming liquid impacting the drive shaft 140.

The priming liquid injected into the relay connector 170 flows toward the distal side through the gap G between the sheath 110 and the support tube 180 (see FIG. 5), and, after passing the distal end of the support tube 180, flows toward the distal side through a gap between the sheath 110 and the drive shaft 140 and is then injected into the lumen 110a (see FIG. 3) of the sheath 110.

As the priming liquid is injected into the lumen 110a, as illustrated in FIG. 3, the priming liquid is discharged to the outside of the sheath 110 via the communicating passage 117a and the communicating hole 116 (see arrows in FIG. 3), so that a gas such as air can be discharged from the inside of the sheath 110 to the outside together with the priming liquid.

After the priming process, as illustrated in FIG. 1, the operator connects the external apparatus 300 to the connector portion 165 (see FIG. 7) of the diagnostic imaging catheter 100. Then, the operator pushes the hub 160 until the hub 160 contacts the proximal end of the unit connector 150 (see FIG. 2A), thus moving the transducer unit 145 toward the distal side as illustrated in FIG. 3. In this state, the sheath 110 is inserted to a target position inside a body cavity (for example, a blood vessel) along the guide wire W while the guide wire W is inserted through the guide wire lumen 114a.

To acquire a tomographic image at the target position inside the body cavity, the transducer unit 145 is moved toward the proximal side (the pullback operation) while being rotated together with the drive shaft 140. At this time, the ultrasound transducer 145a of the transducer unit 145 transmits and receives ultrasound waves. Here, since the support tube 180 covers the drive shaft 140 at the injection opening 173a, the drive shaft 140 can be prevented from entering the injection opening 173a and winding in a twisted or contorted shape.

The rotation and movement operations of the drive shaft 140 are controlled by the control apparatus 320. The connector portion 165, which is provided inside the hub 160, is rotated in the state of being connected to the external apparatus 300, and the drive shaft 140 is rotated in conjunction with the connector portion 165. The rotational speed of the connector portion 165 and the drive shaft 140 is, for example, 1,800 revolutions per minute (rpm).

Furthermore, the ultrasound transducer 145a transmits ultrasound waves into the body based on a signal sent from the control apparatus 320. A signal corresponding to ultrasound waves received by the ultrasound transducer 145a is sent to the control apparatus 320 via the drive shaft 140 and the external apparatus 300. The control apparatus 320 generates a tomographic image of the body cavity based on the signal sent from the ultrasound transducer 145a, and displays the generated image on the monitor 330.

As described above, the diagnostic imaging catheter 100 according to the exemplary embodiment includes the drive shaft 140 which is provided with the ultrasound transducer 145a at a distal portion thereof and which is rotatable and movable forward and backward, the sheath 110 into which the drive shaft 140 is inserted, the relay connector 170 which is coupled to a proximal end of the sheath 110, the support tube 180 which is provided at an outer circumference of the drive shaft 140 along an axial direction thereof and which moves forward and backward in conjunction with the drive shaft 140, the X-ring 175 which is provided inside the relay connector 170 and which seals a space between the relay connector 170 and the support tube 180, and the injection opening 173a which is located in a region closer to a distal side than the X-ring 175 and closer to a proximal side than a distal end (a position indicated by reference character B in FIG. 5) of the support tube 180 in a backward movement limit position thereof and via which a priming liquid is able to be injected into the sheath 110. According to the diagnostic imaging catheter 100 configured as mentioned above, the priming liquid is injected via the injection opening 173a, which is provided in a region closer to the distal side than the X-ring 175 provided inside the relay connector 170. Therefore, the length of the flow path through which the priming liquid flows up to the communicating hole 116 is short as compared with a configuration in which a port is provided at a unit connector or a hub, so that the flow path resistance is reduced. Accordingly, the flow path resistance is decreased without increasing a gap between the sheath 110 and the drive shaft 140, so that the priming process can be smoothly performed. Moreover, since the injection opening 173a is located closer to the proximal side than the distal end (a position indicated by reference character B in FIG. 5) of the support tube 180 in the backward movement limit position, when the priming liquid is injected via the injection opening 173a, the priming liquid contacts the support tube 180 provided on the outer circumference of the drive shaft 140. Accordingly, the priming liquid can be prevented from contacting the drive shaft 140 which can hinder appropriately acquiring an image. With the above-described configuration, the diagnostic imaging catheter 100 can be provided which allows the priming process to be smoothly performed by reducing the flow path resistance without increasing a gap between the sheath 110 and the drive shaft 140, while preventing the priming liquid from contacting the drive shaft 140 to hinder appropriately acquiring an image.

Furthermore, for example, in the case of a configuration in which a port is provided at a hub and a metallic pipe body in a sparsely wound coil shape is located between a drive shaft and an inner shaft, when the priming liquid flows through the pipe body in the coil shape, air bubbles occur due to a difference in speed between the inner circumference and outer circumference of the pipe body. Then, the air bubbles may attach to the transducer unit 145 (air trap) as mentioned above, so that an image may not be able to be appropriately acquired. However, in the case of the diagnostic imaging catheter 100 according to the exemplary embodiment of the disclosure, since a pipe body in a sparsely wound coil shape is not provided, the occurrence of the above air bubbles can be prevented. Accordingly, the occurrence of an air trap can be prevented, and an image can be adequately acquired.

Moreover, the injection opening 173a is provided at the relay connector 170. According to this configuration, the length of the flow path through which the priming liquid flows up to the communicating hole 116 is short as compared with a configuration in which a port is provided at a unit connector or a hub, so that the flow path resistance is reduced. Accordingly, the flow path resistance is decreased without increasing a gap between the sheath 110 and the drive shaft 140, so that the priming process can be smoothly performed.

Additionally, in a case where the lesion area is, for example, a peripheral site such as a foot, since the length of the flow path through which the priming liquid flows is relatively large, providing the injection opening 173a at the relay connector 170, as in the diagnostic imaging catheter 100 according to the exemplary embodiment of the disclosure, enables more adequately reducing the flow path resistance.

Further, the injection opening 173a is located closer to the proximal side than the center of the relay connector 170. According to this configuration, the injection opening 173a is configured to be located closer to the X-ring 175 in the axial direction than in a case where the injection opening 173a is located closer to the distal side than the center of the relay connector 170. Therefore, entrapment of air between the injection opening 173a and the X-ring 175 can be reduced.

Furthermore, the sealing member 164a, which is provided inside the hub 160 located on the proximal side of the relay connector 170 and operable to rotate and move the drive shaft 140 forward and backward, restrains the priming liquid and air (air bubbles) from moving toward the proximal side. According to this configuration, during the priming process, the priming liquid can be prevented from flowing toward the proximal side and contacting the rotor 167. Moreover, air bubbles present in a lumen between the injection opening 173a and the sealing member 164a can be prevented from moving toward the proximal side beyond the sealing member 164a.

Additionally, the port 173 which is coupled to the injection opening 173a is further included, and the port 173 is configured to be inclined from the direction perpendicular to the axial direction toward the proximal side. According to this configuration, when the priming liquid is injected, the priming liquid is enabled to smoothly flow through the injection opening 173a toward the distal side, as compared with a configuration in which a port is provided along the direction perpendicular to the axial direction. Therefore, the force with which the operator pushes the syringe S can be decreased.

Figure 8:
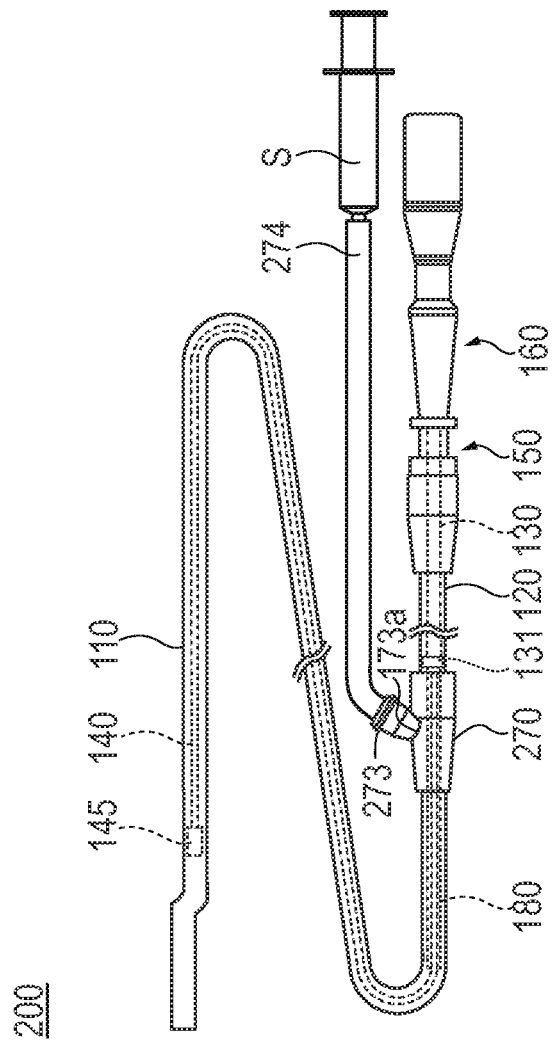
FIG. 8 is a diagram schematically illustrating the entire configuration of a diagnostic imaging catheter according to a further exemplary embodiment of the disclosure.

FIG. 8 is a diagram illustrating the entire configuration of a diagnostic imaging catheter 200 according to a further exemplary embodiment of the disclosure here.

The diagnostic imaging catheter 200 according to the further exemplary embodiment of the disclosure differs in the position where the syringe S is connected from the diagnostic imaging catheter 100 according to the above-described exemplary embodiment.

The diagnostic imaging catheter 200 according to the modification example 1 includes, as illustrated in FIG. 8, a sheath 110, an outer tube 120, an inner shaft 130, a drive shaft 140, a relay connector 270, a support tube 180, a unit connector 150, and a hub 160. The sheath 110, the outer tube 120, the inner shaft 130, the drive shaft 140, the support tube 180, the unit connector 150, and the hub 160 have respective configurations similar to those in the above-described embodiment, and the description thereof is, therefore, omitted.

The relay connector 270 includes a port 273, which is coupled to the injection opening 173a through which the priming liquid is able to be injected. A tube 274 extending toward the proximal side in the axial direction is coupled to the port 273.

With the diagnostic imaging catheter 200 according to the further exemplary embodiment of the disclosure configured in this way, even in a case where it is difficult to connect the syringe S in the vicinity of the port 273, the priming liquid can be injected with the syringe S connected to the tube 274, which extends toward the proximal side.

While diagnostic imaging catheters according to the disclosure have been described through the use of an exemplary embodiment and a further exemplary embodiment, the disclosure is not limited to only the configurations described in the exemplary embodiments, but can have configurations that are changed or altered as appropriate based on the claims.

For example, while, in the diagnostic imaging catheter 100 according to the above-described exemplary embodiment, the injection opening 173a is provided at the relay connector 170, this is not so limiting as long as the injection opening 173a is provided in a region closer to the distal side than the X-ring 175.

Furthermore, while, in the diagnostic imaging catheter 100 according to the above-described exemplary embodiment, the port 173 is formed integrally with the outer tube holding portion 171, the port 173 can be formed integrally with the anti-kink protector 172. Additionally, the port 173 can be configured as a member separate from the anti-kink protector 172 or the outer tube holding portion 171.

Moreover, in the diagnostic imaging catheter 100 according to the above-described exemplary embodiment, the injection opening 173a is located closer to the proximal side than the center of the relay connector 170. However, the injection opening 173a can be located closer to the distal side than the center of the relay connector 170.

Furthermore, in the diagnostic imaging catheter 100 according to the above-described exemplary embodiment, the port 173 is configured to be inclined from the direction perpendicular to the axial direction toward the proximal side. However, the port 173 can be configured to extend in the direction perpendicular to the axial direction.

Moreover, in the above-described exemplary embodiment, the priming liquid is injected into the relay connector 170 by the operator pushing the plunger of the syringe S. However, the priming liquid can be injected into the relay connector 170 by the plunger of the syringe S being pushed by a mechanical configuration and operation.

Additionally, while, in the above-described exemplary embodiment, a diagnostic imaging catheter for use in intravascular ultrasound (IVUS) is taken as an example of an application target for a diagnostic imaging catheter according to the disclosure, the disclosure herein can also be applied to, for example, a diagnostic imaging catheter for use in optical coherence tomography (OCT) and a hybrid-type (dual-type) diagnostic imaging catheter usable in both intravascular ultrasound and optical coherence tomography.

The detailed description above describes features and aspects of an embodiment of a diagnostic imaging catheter. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A diagnostic imaging catheter comprising:
   a sheath;
   a drive shaft provided with a signal transmitting and receiving unit at a distal portion thereof, which is configured to be inserted into the sheath, and which is rotatable and movable forward and backward relative to the sheath;
   a relay connector coupled to a proximal end of the sheath;
   a support tube provided at an outer circumference of the drive shaft along an axial direction and which moves forward and backward in conjunction with the drive shaft;
   a seal member provided inside the relay connector and which seals a space between the relay connector and the support tube; and
   an injection opening which is located in a region closer to a distal side of the catheter than the seal member and closer to a proximal side of the catheter than a distal end of the support tube when the support tube is in a backward movement limit position and via which a liquid is able to be injected into the sheath.

2. The diagnostic imaging catheter according to claim 1, wherein the injection opening is provided in the relay connector.

3. The diagnostic imaging catheter according to claim 2, wherein the injection opening is located closer to the proximal side than a center of the relay connector in the axial direction.

4. The diagnostic imaging catheter according to claim 1, further comprising a sealing member which is provided inside a hub located on a proximal side of the relay connector and operable to rotate and move the drive shaft forward and backward and which restrains the liquid from moving toward the proximal side of the catheter.

5. The diagnostic imaging catheter according to claim 1, further comprising a port which communicates with the injection opening,
   wherein the port is configured to be inclined from a direction perpendicular to the axial direction toward the proximal side of the catheter.

6. The diagnostic imaging catheter according to claim 5, further comprising a tube which communicates with the injection opening via the port and which extends along the axial direction.

7. The diagnostic imaging catheter according to claim 5, wherein the port is integrally formed with the relay connector.

8. The diagnostic imaging catheter according to claim 1, further comprising an outer tube provided at a proximal side of the sheath, the relay connector interconnecting the sheath and the outer tube.

9. The diagnostic imaging catheter according to claim 8, wherein the relay connector includes an outer tube holding portion provided on a proximal side of the relay connector and an anti-kink protector provided on a distal side of the relay connector.

10. The diagnostic imaging catheter according to claim 9, wherein the seal member seals a space between the outer tube holding portion and the support tube.

11. A diagnostic imaging catheter comprising:
a sheath including a lumen;
a drive shaft including a signal transmitting and receiving unit at a distal portion thereof, the drive shaft configured to be inserted in the lumen of the sheath and be rotatable and movable forward and backward relative to the sheath;
a relay connector coupled to a proximal end of the sheath;
a support tube provided around an outer circumference of the drive shaft along an axial direction, the support tube being movable forward and backward in conjunction with the drive shaft from a forward movement limit position to a backward movement limit position;
a seal member provided inside the relay connector, the seal member configured to seal a space between the relay connector and the support tube; and
an injection opening configured for fluid to be injected therethrough and into the sheath,
wherein, when the support tube is in the backward movement limit position, the injection opening is located closer to a distal side of the catheter than the seal member and closer to a proximal side of the catheter than a distal end of the support tube, whereby fluid injected through the injection opening contacts the support tube provided around the outer circumference of the drive shaft rather than directly contacting the drive shaft.

12. The diagnostic imaging catheter according to claim 11, wherein the seal member comprises an X-ring.

13. The diagnostic imaging catheter according to claim 11, further comprising a hub located on a proximal side of the relay connector and operable to rotate and move the drive shaft forward and backward.

14. The diagnostic imaging catheter according to claim 11, wherein the sheath includes a discharge hole formed at a distal portion thereof such that fluid injected into the sheath through the injection opening can be discharged from the sheath via the discharge hole.

15. The diagnostic imaging catheter according to claim 11, further comprising a port configured to communicate with the injection opening, the port being inclined from a direction perpendicular to the axial direction toward the proximal side of the catheter.

16. The diagnostic imaging catheter according to claim 15, wherein the port is integrally formed with the relay connector.

17. A method of using a diagnostic imaging catheter comprising the steps of:
providing a diagnostic imaging catheter including a sheath including a lumen; a drive shaft including a transducer unit at a distal portion thereof, the drive shaft configured to be inserted in the lumen of the sheath and be rotatable and movable forward and backward relative to the sheath; a relay connector coupled to a proximal end of the sheath; a support tube provided around an outer circumference of the drive shaft along an axial direction, the support tube being movable forward and backward in conjunction with the drive shaft from a forward movement limit position to a backward movement limit position; an injection opening configured for fluid to be injected therethrough and into the sheath; a port which communicates with the injection opening; and a hub located on a proximal side of the relay connector and operable to rotate and move the drive shaft forward and backward;
pulling the hub toward a proximal side of the catheter to a maximum extent;
connecting a syringe filled with a fluid to the port;
pushing a plunger of the syringe such that the fluid is injected into the relay connector via the injection opening;
discharging the fluid outside of the sheath via a discharge hole in the sheath; connecting a connector portion of the diagnostic imaging catheter to an external apparatus;
pushing the hub toward a distal side of the catheter to a maximum extent and moving the transducer unit toward a distal side of the sheath;
inserting the sheath to a target position inside a body cavity;
acquiring a tomographic image at the target position by moving the transducer unit toward the proximal side of the catheter in a pullback operation while being rotated together with the drive shaft;
wherein the drive shaft is covered by the support tube at the injection opening during the pullback operation, thereby preventing the drive shaft from entering the injection opening;
wherein the diagnostic imaging catheter further comprises a seal member provided inside the relay connector, the seal member configured to seal a space between the relay connector and the support tube; and
wherein, when the support tube is in the backward movement limit position, the injection opening is located closer to a distal side of the catheter than the seal member and closer to a proximal side of the catheter than a distal end of the support tube, wherein the fluid injected through the injection opening contacts the support tube provided around the outer circumference of the drive shaft rather than directly contacting the drive shaft.

18. The method of using a diagnostic imaging catheter according to claim 17, wherein the external apparatus utilizes intravascular ultrasound.

19. The method of using a diagnostic imaging catheter according to claim 17, further comprising providing the port at an incline toward the proximal side of the catheter from a direction perpendicular to the axial direction.

* * * * *